United States Patent [19]

DeLuca et al.

[11] 4,217,288
[45] Aug. 12, 1980

[54] ANTI-VITAMIN D COMPOUNDS

[75] Inventors: Hector F. DeLuca; Heinrich K. Schnoes; Bruce L. Onisko, all of Madison, Wis.

[73] Assignee: Wisconsin Alumni Research Foundation, Madison, Wis.

[21] Appl. No.: 907,893

[22] Filed: May 19, 1978

Related U.S. Application Data

[63] Continuation-in-part of Ser. No. 781,008, Mar. 24, 1977, abandoned.

[51] Int. Cl.$^2$ ................................................ C07J 9/00
[52] U.S. Cl. ............................... 260/397.2; 260/239.5
[58] Field of Search ..................................... 260/397.2

[56] References Cited

U.S. PATENT DOCUMENTS

| | | | |
|---|---|---|---|
| 3,661,939 | 5/1972 | Toyoda et al. | 260/397.2 |
| 3,665,020 | 5/1972 | Marbet | 260/397.2 |
| 3,833,622 | 9/1974 | Babcock et al. | 260/397.2 |

*Primary Examiner*—Elbert L. Roberts
*Attorney, Agent, or Firm*—Howard W. Bremer

[57] ABSTRACT

25-Aza-vitamin $D_3$, 25-methylvitamin $D_3$, cholanocalciferol dimethylamide and methods for preparing the same. The compounds are characterized by anti-vitamin D activity and find application where inhibition of the intestinal calcium transport or bone calcium mobilization effects of vitamin D are desirable.

10 Claims, No Drawings

ANTI-VITAMIN D COMPOUNDS

The invention described herein was made in the course of work under a grant or award from the Department of Health, Education, and Welfare.

This application is a continuation-in-part of application Ser. No. 781,008, filed Mar. 24, 1977.

This invention relates to compounds which are characterized by anti-vitamin D activity.

More specifically, this invention relates to analogs of vitamin D which exhibit anti-vitamin D activity.

Still more specifically this invention relates to analogs of vitamin D, which, when co-administered to an animal with vitamin D will inhibit or abolish the normal response of that animal to vitamin D.

The application of various of the D vitamins to correct certain calcium metabolism disfunctions, e.g. rickets has long been known. More recently, various derivatives of vitamin D, such as 25-hydroxycholecalciferol (U.S. Pat. No. 3,565,924), 1α-hydroxycholecalciferol (U.S. Pat. No. 3,741,996) and 1,25-dihydroxycholecalciferol (U.S. Pat. No. 3,697,559) permits the treatment of other metabolic disorders involving the calcium and phosphorous balance (imbalance) in animals (see, for example, U.S. Pat. Nos. 3,646,203, 3,639,596 and 3,879,548).

Other derivatives of vitamin D have now been found which are characterized by anti-vitamin D activity. In other words, such compounds, when co-administered with vitamin D tend to abolish the normal response of an animal to vitamin D, that is, they display an inhibitory action against the intestinal calcium transport and bone calcium mobilization effects of vitamin D. Such activity suggests their application for correcting certain calcium disorders in animals such as hypercalcemia, hypervitaminosis D, hypersensitivity to vitamin D and metastatic calcification.

The preferred compounds of this invention have the general formula

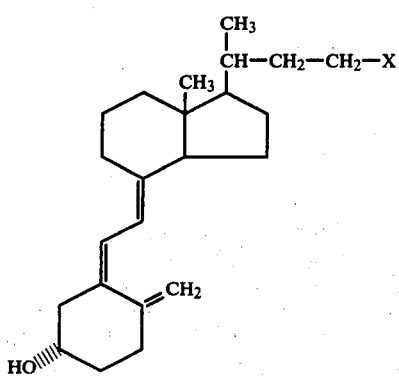

where X is selected from the group consisting of

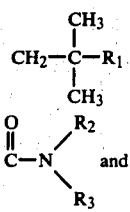

where $R_1$ is lower alkyl and $R_2$ and $R_3$ are each hydrogen, lower acyl, lower alkyl, or aryl.

The terms lower alkyl and lower acyl are intended to designate alkyl and acyl substituents containing from one to about four carbon atoms such as, for example, methyl, ethyl, propyl, etc., or acetyl, propionyl, etc., respectively. The aryl substituent would preferably be a phenyl or substituted phenyl group. It is also to be understood that each of $R_2$ and $R_3$ can be the same or a different one of the substituents above enumerated.

Since it is commonly known that esterified forms of vitamin D are readily hydrolyzed by esterases within the animal body to the free vitamin (Sebrell & Harris, "The Vitamins", Vol. II, Academic Press, N.Y. (1954) p. 143) the esterified forms of the foregoing compounds are also considered to be within the scope of the present invention. Such compounds are represented by the formula:

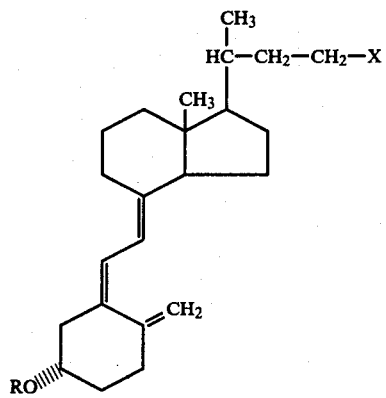

where
X is defined as above and
R is an acyl group having from one to about six carbon atoms or benzoyl.

These compounds can be readily prepared by reaching the particular vitamin D derivatives, i.e., compounds of the formula immediately above where R is hydrogen, with the appropriate acid chloride or acid anhydride, e.g., acetyl chloride or acetic anhydride where the acetic acid ester of the particular compound is desired, in the presence of an organic base.

It is well established that the biological activity of the D vitamins, and specifically vitamin $D_2$ and $D_3$, depends upon their conversion to the 25-hydroxylated form which is an obligatory intermediate in the metabolism of the D vitamin in the animal body. Therefore, any agent which would prevent, in vivo, the hydroxylation of the D vitamins at the C-25 position of the molecule would render the vitamins biologically inactive to perform the known vitamin D functions.

Thus, and although there is no intent to be bound by theoretical considerations, it is believed that the biological properties, i.e., the anti-vitamin D properties, of the componds of this invention are derived from the inability of the substituent group indicated in the C-25 position (or the position corresponding in a formal sense to the C-25 position) in the molecule, to be hydroxylated by the 25-hydroxylase enzyme—the enzyme which normally converts vitamin D to 25-hydroxy vitamin D in the animal body.

The following descriptions directed to the preparation and biological activity of the compounds of this invention, are to be considered illustrative only and are not to be construed as imposing any limitations upon the following claims.

In the description and in the following schematics specific compounds are identified by like numeric designations.

(45), 281 (28), 91 (100); homogeneous on tlc ($R_f$=0.50, 20% ethyl acetate in Skellysolve B).

(20-S)-20-Bromomethyl-6β-methoxy-3α-5-cyclo-5α-pregnane (2)

2.30 grams of the tosylate (1), in 314 ml acetonitrile, and 3.51 g of dry, powdered lithium bromide was heated at reflux for 6.5 hr. After removal of the solvent by flash evaporation, the solids were dissolved in 150 ml $H_2O$ and extracted three times with 50 ml each of dichloromethane. The combined extracts were washed twice with 50 ml $H_2O$, once with 50 ml saturated salt,

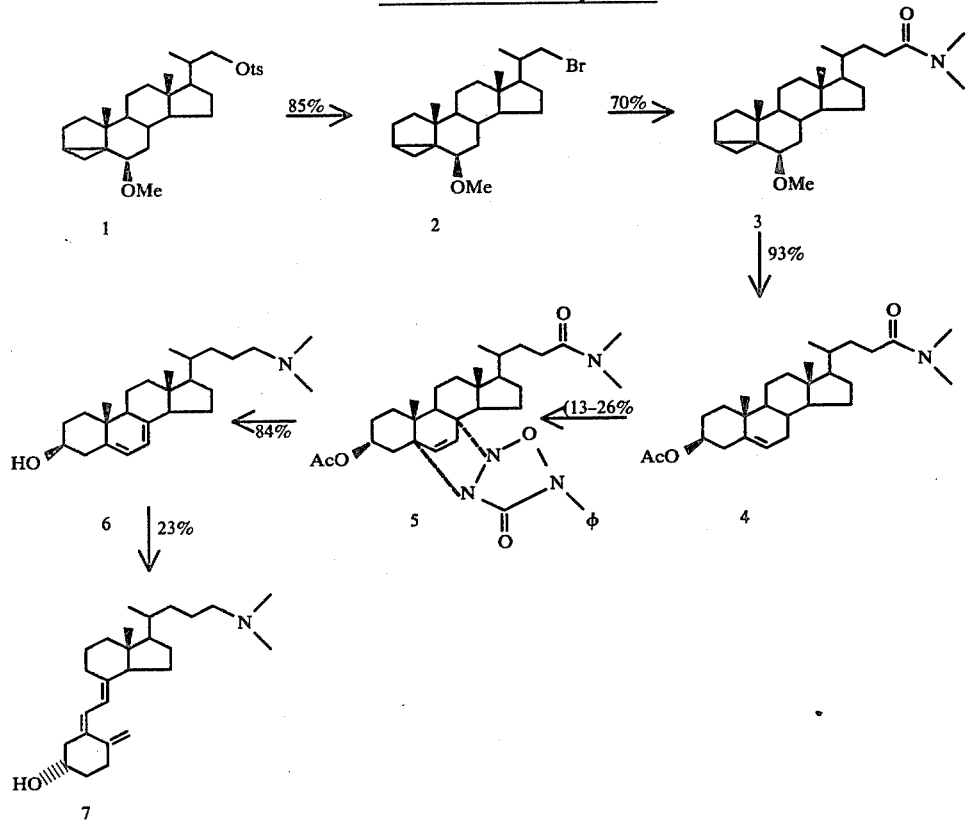

(1)
Process Schematic for Preparing
25-aza-vitamin $D_3$

25-Aza-Vitamin $D_3$

Detailed Description of the Synthesis of the Process Schematic (1)

(20-S)-6β-Methoxy-20(p-toluenesulfonoxymethyl)-3α,5-cyclo-5α-pregnane (1)

Starting material 1 was prepared from stigmasterol in overall yield of 61% according to the procedure of J. J. Partride, S. Faber, and M. R. Uskokovic (Helv. Chim. Acta 57, 764 (1974)). It had the following physical properties: mp 144°-145°; $[\alpha]_D^{20}=+34$ (C 98, $CHCl_3$); ir ($CCl_4$) 1190 and 1180 cm$^{-1}$ (sulfonate), 1100 cm$^{-1}$ (C-O for i-ether); nmr ($CDCl_3$) δ 7.79 and 7.34 (AB, 4H, $J_{AB}$=8 Hz, tosylate) 3.98 (d of d, $J_1$=9.0, $J_2$=3.4 Hz, 1H, 22$\epsilon_1$), 3.78 (d of d, $J_1$=9.0, $J_2$=5.9 Hz, 1H, 22$\epsilon_2$), 3.31 (s, 3H, O-Me), 2.76 (d of d, $J_1$=$J_2$=2.7 Hz, 1H, 6α-H), 2.45 (s, 3H, tosylate), 1.01 (s, 3H, C-19), 0.98 (d, J=6 Hz, 3H, C-21), 0.68 (s, 3H, C-18), 0.42 (d of d, $J_1$=7.8, $J_2$=4.8 Hz, 1H, C-4α); mass spectrum m/e (rel. intensity) 500 (M+, 19), 485 (12), 468 (68), 445 (21), 296 dried over sodium sulfate and flash evaporated. Crystallization from aqueous ethanol gave 1.88 g (85%) of 2; mp 63.5°-65°; $[\alpha]_D^{20}=+55°$ (C 1.60, $CHCl_3$); ir ($CCl_4$) 1100 cm$^{-1}$ (C-O for i-ether); nmr ($CDCl_3$) δ 3.52 (d of d, $J_1$=9.8, $J_2$=2.8 Hz, 1H, C-22$\epsilon_1$) 3.34 (d of d, $J_1$=9.8, $J_2$=5.4 Hz, 1H, C-22$\epsilon_2$), 3.32 (s, 3H, O-Me), 2.77 (d of d, $J_1$=$J_2$=2.9 Hz, 1H, C-6α), 1.09 (d, J=6.3 Hz, 3H, C-21), 1.02 (s, 3H, C-19), 0.75 (s, 3H, C-18), 0.68 (d of d, $J_1$=7.9, $J_2$=4.0 Hz, 1H, C-4β), 0.43 (d of d, $J_1$=7.9, $J_2$=5.0 Hz, 1H, C-4α); mass spectrum, m/e (rel. intensity) 410 (52), 408 (48), 395 (40), 393 (42), 378 (98), 376 (100), 355 (78), 353 (85); homogeneous on tlc ($R_f$=0.70, 10% ethyl acetate in Skellysolve B); 98% pure by glc ($t_r$=4.1 min); Anal. Calcd. for $C_{23}H_{37}OBr$: C, 67.47; H, 9.11. Found: C, 67.49; H, 9.23.

6β-Methoxy-3α,5-cyclo-5α-cholanic acid dimethylamide (3)

4.9 ml of 1.79 M n-butyl lithium was added to a dry flask charged with 14.5 ml tetrahydrofuran, 3.6 ml hexane, and 1.55 ml diisopropylamine. The mixture was maintained under $N_2$ at 0° C. for 0.5 hours after which the flask was cooled to −78° C., 1.63 ml dimethylacetamide was added, and the mixture was stirred at −78° C. for 1.25 hours. The bromide (2, 1.2 g in 15 ml tetrahydrofuran) was added, and the mixture stirred at 0° C. for 21 hours. After adding a few chips of ice followed by 50 ml 5% HCl, the mixture was extracted three times with dichloromethane (50 ml for each extraction). The organic extracts were combined and washed with saturated salt, dried over sodium sulfate and flash evaporated. The residue was chromatographed on a 250 g column of silica gel. Elution with ethyl acetate afforded (pool tubes 34 to 67, 15 ml fractions) 0.85 g (70%) of 3 as a clear oil, which resisted crystallization. The oil showed: ir (CCl$_4$) 1655 cm$^{-1}$ (amide), 100 cm$^{-1}$ (C-O) of i-ether); nmr (CDCl$_3$) δ 3.32 (s, 3H, O-Me), 3.00 (s, 3H, N-Me), 2.93 (s, 3H, N-Me), 2.77 (d of d, $J_1=J_2=2.9$ Hz, 1H, C-6α), 1.02 (s, 3H, C-19), 0.94 (d, J=5.9 Hz, 3H, C-21), 0.72 (s, 3H, C-18), 0.43 (d of d, $J_1=8.3$, $J_2=4.8$ Hz, 1H, C-4α); mass spectrum m/e (rel. intensity) 415 (M+, 6), 400 (7), 383 (26), 368 (8), 360 (13), 100 (32), 87 (100); high resolution mass spectrum Calcd. for $C_{27}H_{95}NO_2$: 415.345; Found: 415.343.

3β-Acetoxy-5-cholenic acid dimethy amide (4)

1.86 g of the cyclosteroid (3) was dissolved in 75 ml glacial acetic acid and the mixture then heated to 70° C. for 18 hours. After cooling to room temperature the mixture was neutralized with 10% aqueous sodium hydroxide and extracted three times with ethyl acetate (100 ml for each extraction). The organic extracts were combined and washed three times with 10% aqueous sodium hydroxide (50 ml for each washing), once with 50 ml of water and once with 50 ml of saturated salt. Flash evaporation gave an amorphous solid that was crystallized from hexane to provide 1.85 g (93%) of 4: mp 192°-193.4°; $[\alpha]_D^{20}=-41°$ (c, 1.1, CHCl$_3$); ir (CCl$_4$) 1733 and 1245 cm$^{-1}$ (acetate), 1651 cm$^{-1}$ (amide); nmr (CDCl$_3$) δ 5.37 (m, 1H, C-6), 4.62 (m, $W_{\frac{1}{2}}=20$ Hz, 1H, C-3α), 3.00 (s, 3H, N-Me), 2.93 (s, 3H, N-Me), 2.03 (s, 3H, acetate), 1.02 (s, 3H, C-19), 0.95 (d, J=5.9 Hz, 3H, C-21), 0.68 (s, 3H, C-18); mass spectrum, m/e (rel. intensity) 443 (M+, 0.8), 428 (0.6), 383 (65), 368 (6), 100 (70), 87 (100); homogeneous on tlc (R$_f$=0.55, ethyl acetate); 96% pure by glc (t$_R$=28.6 min); Anal. Calcd. for $C_{28}H_{45}NO_3$: C, 75.80; H, 10.22; N, 3.16. Found: C, 75.70; H, 10.30; N, 3.09.

4-Phenyl-1,2,4-triazolin-3,5-dione adduct of 3β-acetoxycholan-5,7-dienoic acid dimethyl amide (5)

A mixture of 500 mg of the amide 4, 45 ml carbon tetrachloride, 665 mg sodium bicarbonate and 194 mg 1,3-dibromo-5,5-dimethylhydantoin was refluxed under nitrogen for 3 hours. After cooling to 0° C., the solid hydantoin was removed by filtration. The filtrate was evaporated, redissolved in 5 ml xylene and added dropwise to a mixture of 300 mg collidine in 65 ml xylene at 140° C. The reaction mixture was maintained at this temperature under N$_2$ for 1.5 hours, cooled to room temperature, diluted with 100 ml benzene, and washed with 50 ml each of 5% HCl, 4% NaHCO$_3$ and saturated salt (NaCl) solution. After drying over Na$_2$SO$_4$ the solvent was evaporated at reduced pressure and the resulting oil was crystallized with 5.0 ml acetone. The resulting crystals, representing both 4,6 and 5,7-dienes, were dissolved in 50 ml ethyl acetate, cooled to 0° C., and titrated with 10.5 ml of a 2 mg/ml solution of 4-phenyl-1,2,4-triazolin-3,5-dione in ethyl acetate. After removing the solvent by evaporation the residue was purified by preparative tlc developed with 3% MeOH in CHCl$_3$. Crystallization from hexane provided 87 mg (13%) of 5: $[\alpha]_D^{20}=-77°$ (C 0.49, CHCl$_3$); uv (EtOH) λ$_{max}$255 nm (ε3,900); ir (CCl$_4$) 1736 and 1242 cm$^{-1}$ (acetate), 1757 and 1705 cm$^{-1}$ (triazoline) 1652 cm$^{-1}$ (amide); nmr (CDCl$_3$) δ 7.39 (M, 5H, phenyl), 6.92 and 6.22 (AB, J=8 Hz, 2H, C-6 and C-7), 5.42 (t of t, $J_1=10$, $J_2=5$ Hz, 1H, C-3α), 3.28 (d of d, $J_1=13$, $J_2=5$ Hz, 1H, C-4α), 3.00 (s, 3H, N-Me), 2.93 (s, 3H, N-Me), 2.01 (s, 3H, acetate,) 0.98 (s, 3H, C-19), 0.95 (d, J=5 Hz, 3H, C-21), 0.81 (s, 3H, C-18); mass spectrum m/e (rel. intensity) 439 (2), 381 (35), 366 (35), 311(11), 177 (22), 100 (33), 87 (100); homogeneous on tlc (R$_f$=0.53, 3% MeOH in CHCl$_3$).

25-aza-7-dehydrocholesterol (6)

76 mg of lithium aluminum hydride was added to a mixture of 61.1 mg of the adduct (5) in 13 ml dry distilled tetrahydrofuran. After refluxing under N$_2$ for 7.0 hours, the reaction was terminated by the addition of 5.0 ml of water. The white precipitate was removed by filtration and washed with dichloromethane; 20 ml of water was added to the filtrate to produce a two-phase system. The organic (lower) layer was removed and the aqueous phase was extracted three times with dichloromethane (20 ml for each extraction). The organic extracts were combined and dried over Na$_2$SO$_4$, the solvents were removed at reduced pressure, and the residue was chromatographed on 75 g of aluminum oxide. Elution with 3% MeOH in CHCl$_3$ gave (in tubes 23 to 34, 3.5 ml fractions) an amorphous solid which, after recrystallization from hexane, provided 32 mg (84%) of 6: mp 141.5°-143°; $[\alpha]_D^{20}=-118$ (c 0.27, CHCl$_3$); uv (EtOH) λ$_{max}$ 252 nm (ε 4,500), 262 (ε 8,100), 271 (ε 11,300), 281 (11,400), 291 (6,400); ir (CHCl$_3$) 3630 cm$^{-1}$ (OH), 2820 and 2780 and 1460 cm$^{-1}$ (R-N-(CH$_3$)$_2$), 1600 and 1655 cm$^{-1}$ (diene), 1040 and 1020 cm$^{-1}$ (C-O); nmr (CDCl$_3$) δ 5.57 (d of d, $J_1=5.9$, $J_2=2.4$ Hz, 1H, C-6), 5.39 (d of t, $J_1=5.8$, $J_2=2.1$ Hz, 1H, C-7), 3.64 (t of t, $J_1=11.1$, $J_2=4.1$ Hz, 1H, C-3α), 2.24 (s, 6H, N-(Me)$_2$), 0.95 (d, J=6 Hz, 3H, C-21), 0.94 (s, 3H, C-19), 0.62 (s, 3H, C-18); mass spectrum m/e (rel. intensity) 385 (M+, 26), 370 (5), 352 (2), 84 (5), 71 (4), 58 (100); homogeneous on tlc (R$_f$=0.64, 3% MeOH in CHCl$_3$, aluminum oxide G); 98% pure by glc (t$_R$=12.4 min, oven=260°); Anal. Calcd for $C_{26}H_{43}NO$: C, 80.98; H, 11.24; N, 3.63. Found: C, 80.81; H, 11.45; N, 3.58; high resolution mass spectrum Calcd. for $C_{26}H_{43}NO$: 385.3345, Found: 385.3350.

25-Azavitamin D$_3$ (7)

The diene 6 (10.0 mg in 100 ml ethyl ether) in an ice bath was irradiated under N$_2$ for 3.25 min with vigorous stirring using a water-cooled quartz irradiation apparatus, and a low pressure mercury arc lamp with a Vycor filter. The solvent was evaporated, and the residue was purified on a 45 g column of Sephadex LH-20 using MeOH as eluent. (Sephadex LH-20 is a hydroxypropyl ether derivative of a polydextran marketed by Pharmacia Fine Chemicals Inc., Piscataway, N.J.) The previtamin derivative (λ$_{max}$ 262) eluted in fractions 37 to 52

(6.5 ml fractions). These fractions were pooled, the solvent was evaporated and the resulting solid was redissolved in 2.0 ml ethanol. After heating to 70° C. under $N_2$ for 2.0 hours, the sample was applied to the same Sephandex LH-20 column and developed with MeOH. Fractions 45 to 72 were pooled providing 2.3 mg (23%) of the desired 25-aza-vitamin $D_3$ (7) as an oil: uv (EtOH)$\lambda_{max}$ 265 nm, $\lambda_{min}$ 230 nm; nmr (CDCl$_3$) $\delta$ 6.24 and 6.03 (AB, J=10.9 Hz, 2H, C-6 and C-7), 5.05 (d of t, $J_1=2$, $J_2=1$ Hz, 1H, C-19), 4.82 (d, J=2 Hz, 1H, C-19), 3.95 (t of t, $J_1=7.4$, $J_2=3.7$ Hz, 1H, C-3$\alpha$), 2.58 (d of d, $J_1=12$, $J_2=3.4$ Hz, 1H, C-4$\alpha$), 2.41 (d of d of d, $J_1=14$, $J_2=7.1$, $J_3=4.9$ Hz, 1H, C-1$\alpha$), 2.31 (s, 6H, N-Me)$_2$), 2.29 (d of d, $J_1=12$, $J_2=7.5$ Hz, 1H, C-4$\beta$), 0.93 (d, J=6 Hz, 3H, C-21), 0.54 (s, 3H, C-18); mass spectrum m/e (rel. intensity) 385 M+, 15), 370 (3), 352 (1), 249 (1), 84 (10), 71 (4), 58 (100); high resolution mass spectrum, Calcd. for $C_{26}H_{43}NO$: 385.3345; found: 385.3340; homogenous on tlc ($R_f$=0.69, 3% MeOH/CHCl$_3$, Aluminum oxide G); >99% pure by glc ($t_r$=9.6 and 10.5 min for pyro and isopyro derivatives at a column temperature of 260° C.).

The 25-aza-vitamin $D_3$ can be readily obtained in crystalline form by dissolving the recovered oil in suitable solvent media and evaporating the solvent from the resulting solution.

butyne (generated with n-butyl lithium) gives the acetylenic intermediate 10. Hydrogenation of 10 ($H_2$, 10% Pd/C) affords 11 which by solvolysis in hot glacial acetic acid is converted to 25-methylcholesterol 3$\beta$-acetate (compound 12). This intermediate acid is allylically brominated and dehydrobrominated to 5,7-diene 13. Irradiation of 13 (3$\beta$-acetoxy-25-methylcholesterol-5,7-diene) followed by thermal isomerization of the isolated previtamin derivative and saponification (KOH/MeOH) leads to 25-methyl vitamin $D_3$ (14).

6$\beta$-Methoxy-25-Methyl-3$\alpha$,5-cyclo-5$\alpha$-cholest-23-yne (10)

25 ml of a 1.5 M solution of n-butyl lithium in hexane is added to a solution of 3 g of 3,3-dimethyl-1-butyne in 120 ml of dioxane at 5°. The mixture is stirred for 4 hours at room temperature, then 6 g (0.015 mol) of bromide 2 is added and the mixture is refluxed for 3 days. Workup gives an oil which is purified on a column of silica gel (500 g). This gives 5.5 g (90%) of alkyne 10 as an oil, sufficiently pure for subsequent steps.

6$\beta$-Methoxy-25-methyl-3$\alpha$,5-cyclo-5$\alpha$-cholestane (11)

A mixture of 5.1 g (0.013 mol) of 10, 75 ml dioxane, 1.0 g of sodium bicarbonate and 0.1 g of 10% Pd/C is stirred under 1 atm of $H_2$ until 2 equiv. of gas are con- (2)
Process Schematic for
Preparing 25-Methylvitamin $D_3$

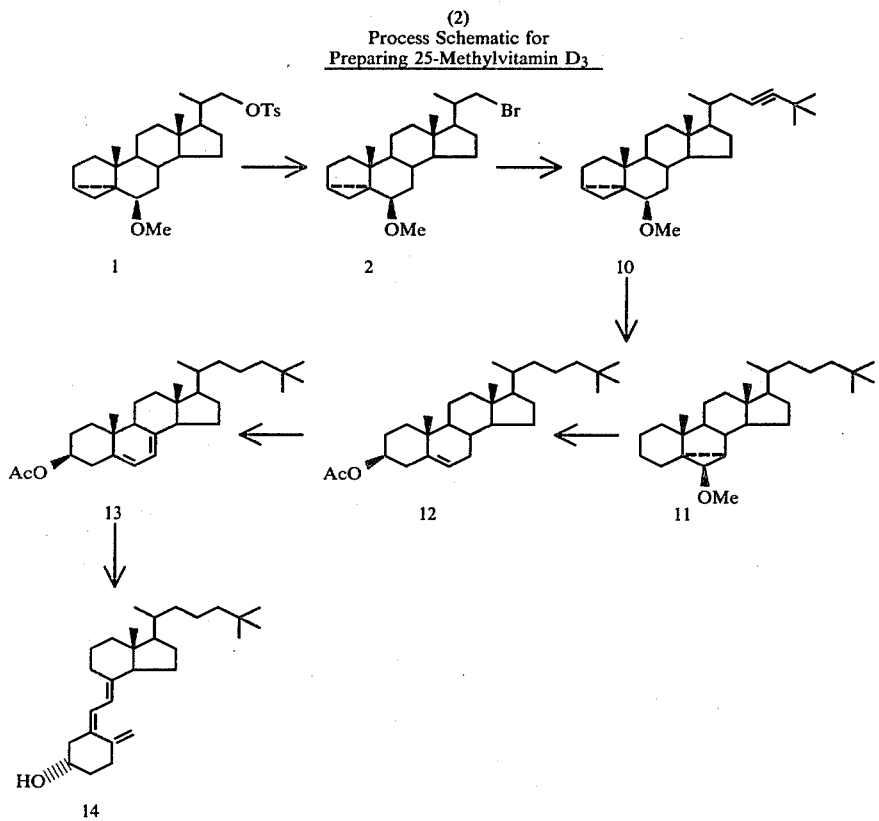

25-Methylvitamin $D_3$

Detailed Description of the Synthesis of Process Schematic (2)

Preparation of the 25-methyl analog 14 is accomplished via a route similar to that used for the synthesis of 25-azavitamin $D_3$ described above. Reaction of bromide 2 in the THF with the lithium salt of 3,3-dimethyl-butyne (generated with n-butyl lithium) sumed. The solids are then removed by filtration and the filtrate is concentrated in vacuo to yield an oil which after purification on a column of silica gel (400 g) yields the 25-methyl derivative 11 (4.75 g, 90%).

Solvolysis of compound 12: Formation of 25-methylcholesterol 3β-acetate (12)

3,5-cyclosteroid 12 (2 mmole), dissolved in 50 ml glacial acetic acid, is heated to 70° for 18 hr. After cooling, the mixture is neutralized with 10% aqueous NaOH and extracted 3 times with ethyl acetate (75 ml each). The organic extracts are combined and washed with 10% aqueous NaOH (3×50 ml), then with saturated salt solution and water. Evaporation of the organic solvent then gives compound 12 as an amorphous solid in 85–90% yield, in sufficient purity for subsequent reaction steps.

3β-acetoxy-25-methylcholesta-5,7-diene (13)

Cholesterol derivative 12 (1 mmole) in 40 ml of $CCl_4$ is treated with 600 mg $NaHCO_3$ and 170 mg of 1,3-dibromo-5,5-dimethyl hydantoin, and the mixture is refluxed under $N_2$ for 3 hours. After cooling to 0° C. the solid hydantoin is removed by filtration. The filtrate is evaporated, the residue is redissolved in 5 ml xylene at 140° C. After 1.5 hours under $N_2$ at this temperature the mixture is cooled to room temperature, diluted with benzene, and washed with 5% HCl, 4% $NaHCO_3$ and saturated NaCl solution. After drying (using $Na_2SO_4$) the solvent is evaporated and the residue is chromatographed on $AgNO_3$-impregnated thin layer plates developed with ethyl acetate/Skellysolve B (1:4). This yields pure 5,7-diene (13) of molecular weight 440 and exhibiting the typical 5,7-diene ultraviolet spectrum.

25-Methylvitamin D₃ (14)

The 5,7-diene 13 (0.02 mmoles, in 100 ml diethyl ether), is irradiated under $N_2$ and in an ice bath for 3 min. with vigorous stirring, using a water-cooled quartz irradiation apparatus and a low-pressure mercury arc lamp with a Vycor filter. The solvent is then evaporated and the residue is purified by preparative thin layer chromatography (ethyl acetate/hexane). The previtamin derivative is recovered and subjected to hydrolysis in 0.1 M KOH/MeOH, at 70° over 3 hours. This step accomplishes both the removal of acetate and the isomerization of the previtamin skeleton to the vitamin compound. The basic medium is diluted with $H_2O$ and extracted with ethyl acetate. After evaporation of the organic solvent, the product is purified on $AgNO_3$ impregnated silica gel plates (ethyl acetate/Skellysolve B). This yields the vitamin analog, 25-methyl-vitamin D₃ (compound 14) in pure form and exhibiting the expected physical properties (molecular weight 398; ultraviolet maximum at 265 nm).

(3)
Process Schematic for Preparing
Cholanocalciferol Dimethyl Amide

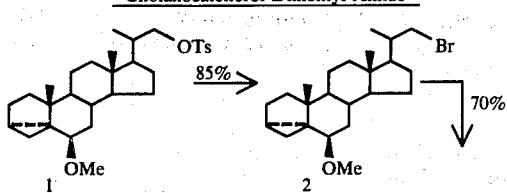

(3)
Process Schematic for Preparing
Cholanocalciferol Dimethyl Amide

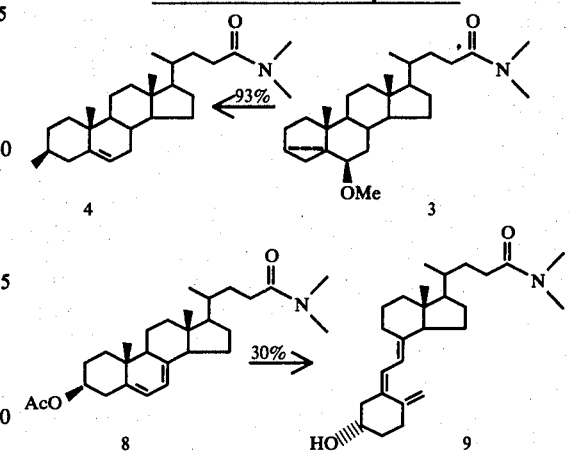

Cholanocalciferol Dimethyl Amide

Detailed Description of the Process Schematic (3)

7-dehydrocholenic acid dimethyl amide 3β-acetate (8)

A mixture of 500 mg of amide 4, 45 ml carbon tetrachloride, 665 mg of sodium bicarbonate and 194 mg of 1,3-dibromo-5,5-dimethylhydantoin is refluxed under $N_2$ for 3 hours. After cooling to 0° C., the precipitated hydantoin is removed by filtration. The filtrate is evaporated, redissolved in 5 ml xylene and added dropwise to a mixture of 300 mg collidine in 65 ml xylene at 140° C. The reaction is maintained at this temperature under $N_2$ for 1.5 hours, cooled to room temperature, diluted with 100 ml benzene, washed with dilute HCl, then $NaHCO_3$ solution and then saturated salt solution. The product is then chromatographed on $AgNO_3$-impregnated silica gel thin layer plates developed with ethyl acetate/Skellysolve B, to yield (20%) pure 5,7-diene (compound 8) of molecular weight 441 and the typical ultraviolet spectrum for a 5,7-diene chromophore.

Irradiation of compound 8: Formation of vitamin analog 9

Diene 8 (0.025 mmole) dissolved in 100 ml diethyl ether, and cooled in an ice bath is irradiated under $N_2$ for 3 min. with vigorous stirring using a water-cooled quartz irradiation apparatus and a low pressure mercury arc lamp with a Vycor filter. The solvent is evaporated and the residue is purified by preparative silica gel thin layer chromatography. The previtamin derivative is collected and subjected to hydrolysis (0.1 M KOH/MeOH, 50°–70°, 3 hr) to affect both hydrolysis of the acetate and thermal isomerization of the previtamin, to the vitamin structure. The hydrolysis mixture is then diluted with $H_2O$, extracted with ethyl acetate, and after evaporation of the solvent, the resulting product is purified on silica gel thin layer plates, developed with ethyl acetate/Skellysolve B. This yields (30%) the amide vitamin analog 9 (cholanocalciferol dimethyl amide) in pure form exhibiting the expected physical properties i.e. molecular weight 399, and ultraviolet maximum at 265 nm.

Synthesis of Cholanocalciferol Dimethylamide (Vitamin Analog 9.)

As shown in process schematic 1 the cholenic acid dimethyl amide derivative 4 also serves as an intermediate for the preparation of the 5,7-diene dimethyl amide 8. Conversion of 4 to 8 is accomplished in the usual manner, namely by allylic bromination and dehydrobromination. Purification of the desired 5,7-diene 8 is accomplished by chromatography on $AgNO_3$-impregnated silica gel. Irradiation of 8 in ether (in precisely the same manner as described for the conversion of 6 to 7) gives the previtamin derivative which after thermal isomerization, saponification (0.1 M KOH/MeOH/70°/3 hr), and purification (silica gel preparation thin layer plates employing 25% ethyl acetate in Skellysolve B) affords the amide vitamin 9 in a homogenous state.

Biological Activity of 25-aza-vitamin $D_3$

The biological properties of 25-aza-vitamin $D_3$ were assayed in the rat using the following experimental protocol:

Male albino weanling rats were housed in overhanging wire cages and fed ad libitum a vitamin D-deficient diet (Suda et al, J. Nutr. 100, 1049–1052 (1970) containing 0.02% calcium and 0.3% phosphorous for two weeks. The rates were then divided randomly into four groups and dosed intrajugularly as indicated in the Table below. The doses administered were 0.05 ml of ethanol or the indicated material in 0.05 ml of ethanol. The second dose was administered two hours after the first dose. Twenty hours after the second dose the rats were sacrificed and calcium transport and serum calcium levels were determined by the methods described in Blunt et al, Proc. Nat'l. Acad. Sci. U.S. 61, 1503 (1968).

Table I

| Experiment | Dose 1 | Dose 2 | Calcium transport ratio ± SE (# rats) | Serium Calcium mg% ± SE (# rats) |
|---|---|---|---|---|
| 1 | ethanol | ethanol | 2.4 ± .1 (7) | 4.6 ± .1 (7) |
| 2 | ethanol | 50 ng $D_3$ | 4.0 ± .1 (8) | 5.6 ± .1 (8) |
| 3 | 50 μg 25-aza-$D_3$ | 50 ng $D_3$ | 2.7 ± .2 (4) | 5.0 ± .2 (4) |
| 4 | ethanol | 50 μg 25 aza-$D_3$ | 1.5 ± .1 (4) | 4.4 ± .1 (4) |

Experiment 1 represents the control experiment (treatment with solvent only). Experiment 2 establishes that vitamin $D_3$, given alone, produces the expected biological response. Experiment 3 establishes that pretreatment of animals with 25-aza-vitamin $D_3$ completely suppresses their biological response to vitamin $D_3$. Experiment 4 shows that 25-aza-vitamin $D_3$ itself does not elicit a vitamin D-like response and may have antagonized remaining endogenous vitamin $D_3$.

It is evident from the foregoing data that 25-aza-vitamin $D_3$ exhibits an anti-vitamin D effect. Such effect, as amply illustrated suggests that this compound can be used to advantage to reduce or reverse the biological effect of the D vitamins or to counteract hypercalcemia. Moreover, and inasmuch as the other compounds of this invention, as described hereinbefore, and as enumerated in the appended claims, like 25-aza-vitamin $D_3$, can inhibit or prevent hydroxylation of the D vitamin molecules at the C-25 position (or the position corresponding in a formal sense to C-25), such compounds will also be characterized by anti-vitamin D activity.

Having thus described the invention what is claimed is:

1. Compounds having the formula

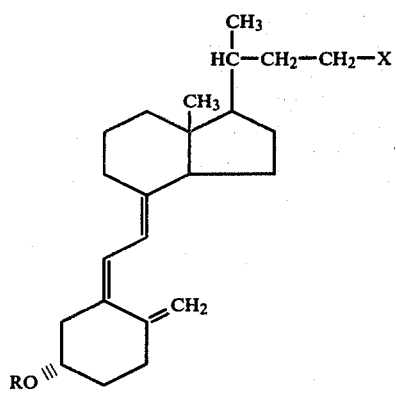

where
X is selected from the group consisting of

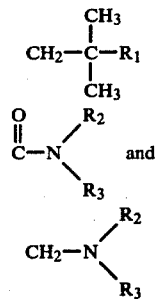

R is selected from the group consisting of hydrogen, an acyl group having from 1 to about 6 carbon atoms and benzoyl,
$R_1$ is lower alkyl and $R_2$ and $R_3$ are each hydrogen, lower alkyl, lower acyl or aryl.

2. The compound of claim 1 wherein
R is hydrogen and

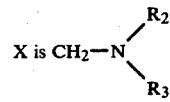

where each of $R_2$ and $R_3$ are methyl.

3. The compound of claim 2 in crystalline form.

4. A method for preparing 25-aza-vitamin $D_3$ which comprises;
halogenating (20-S)-6β-methoxy-20 (p-toluenesulfonoxymethyl)-3α,5-cyclo-5α-pregnane (1) with a reactant selected from the group consisting of lithium bromide or lithium iodide;
condensing the resulting halogenated product with dimethylacetamide in the presence of a strong base to produce the corresponding cholenic acid dimethylamide;

heating the resulting condensation product with glacial acetic acid to obtain the corresponding acetylated cholenic acid dimethylamide;

treating the said cholenic acid dimethylamide consecutively with 1,3-dibromo-5,5-dimethyl-hydantoin and collidine and recovering the resulting crystalline product comprising a mixture of 3β-acetoxycholan-5,7- and 3β-acetoxycholan-4,6-dieonic acid dimethyl amides;

isolating the 5,7-diene compound by Diels-Alder adduct formation with 4-phenyl-1,2,4-triazolin-3,5-dione;

reducing the adduct with a hydride reducing agent and recovering 25-aza-7-dehydrocholesterol;

subjecting the said 25-aza-7-dehydrocholesterol to ultraviolet irradiation and recovering 25-aza-previtamin $D_3$;

heating the said previtamin to convert it to 25-aza-vitamin $D_3$ and recovering the 25-aza-vitamin $D_3$.

5. 25-aza-7-dehydrocholesterol.

6. 25-aza-previtamin $D_3$.

7. 7-dehydrocholenic acid dimethyl amide 3β-acetate.

8. Cholanocalciferol dimethylamide.

9. 3β-acetoxy-25-methylcholesta-5,7-diene.

10. 25-methylvitamin $D_3$.

* * * * *